United States Patent [19]

Rona

[11] 3,932,306

[45] Jan. 13, 1976

[54] SOLID CATALYST FOR HETEROGENEOUS REACTIONS
[75] Inventor: Peter Rona, Haifa, Israel
[73] Assignee: IMI (TAMI) Institute for Research & Development, Haifa, Israel
[22] Filed: Jan. 4, 1974
[21] Appl. No.: 431,010

[30] Foreign Application Priority Data
Jan. 17, 1973  Israel..................................... 41329

[52] U.S. Cl. ............... 252/430; 252/426; 252/428; 260/497 R; 260/614 R; 260/641; 260/671 C
[51] Int. Cl.$^2$.......................................... B01J 31/02
[58] Field of Search.................... 252/428, 430, 426

[56] References Cited
UNITED STATES PATENTS

| | | | |
|---|---|---|---|
| 2,772,317 | 11/1956 | Smith et al..................... | 252/428 X |
| 3,146,246 | 8/1964 | Goodrich........................ | 252/428 X |
| 3,172,905 | 3/1965 | Eckert ........................... | 252/426 X |

*Primary Examiner*—Patrick P. Garvin
*Attorney, Agent, or Firm*—Ladas, Parry, Von Gehr, Goldsmith & Deschamps

[57] ABSTRACT

Catalyst for carrying out heterogeneous catalytic chemical reactions. The catalyst is a composite comprising a solid carrier and at least one member of the group of carboxymethane sulfonic acid and products resulting from the thermal treatment thereof at a temperature not exceeding 350°C. The catalyst is prepared by impregnating the carrier carboxymethane sulfonic acid or a precursor or precursors thereof, drying the impregnated carrier at a temperature not exceeding 170°C and baking the so dried product at 170° to 330°. Examples of catalytic reactions that are successfully carried out with such a catalyst are production of alcohols by hydration of olefins, production of esters from acids and olefins, production of esters from alcohols and alkylation of aromatic hydrocarbons.

9 Claims, No Drawings

SOLID CATALYST FOR HETEROGENEOUS REACTIONS

The present invention concerns acidic catalysis of organic reactions. More particularly, the invention concerns acidic solid catalysts for heterogeneous acidic catalysis of organic reactions, i.e., reactions that proceed in the vapour phase in the presence of a solid catalyst.

Examples of organic reactions which are promoted by acidic catalysis and in respect of which the present invention is applicable are hydration of olefins, dehydration of alcohols to olefins and/or to ethers, formation of esters from olefins and acids, alkylation, arylation, isomerization and polymerization of olefins, alkylation of phenols to ethers and alkylphenols. These examples are not meant to limit in any way the scope of applicability of the present invention.

For acidic catalysis in solution it is quite common to use sulfonic acids which combine good solubility with a strong acidity. For example, para-toluene sulfonic acid is an extremely versatile acid catalyst used in solution to promote a host of acid catalysed reactions such as trans-esterification, enol-ether formation, ketalysation, acetylation, dehydration, isomerization, etc. Furthermore, methane di-sulfonic acid and methane tri-sulfonic acid have been stated to catalyse the alkylation of phenols in solution.

In many cases heterogeneous catalysis by solid catalysts is advantageous, among others for the reason that from a heterogenous system the catalyst is easily regained and also the recovery of the product is simpler than in the case of a homogeneous system. Indeed many acidic solid catalysts are known, both of the type in which the acidity stems from the chemical composition of the solid and of the type in which the acidity is the consequence of the presence of a liquid acid adsorbed to the surface of an inert solid carrier. Thus there are known catalysts prepared by the adsorption of phosphoric acid onto the surface of inert solids and such catalysts are used, for example, in the manufacture of alcohols by direct hydration of olefins, and in the alkylation, arylation and polymerization of olefins. These catalysts are not entirely satisfactory since they tend to lose some of their catalytic activity as a consequence of the depletion of the phosphoric acid content of the solid, due to entrainment of some of the phosphoric acid in the gas streams carrying the reactants, which in turn is the result of the loose-type association which generally exists between the phosphoric acid and the solid carrier.

A similar difficulty has been observed with known catalysts consisting of boron trifluoride adsorbed on anhydrous inorganic oxides.

The decrease in the concentration of the adsorbed acidic component in this type of catalyst, caused by the entrainment of the acidic component in the reacting gas streams reduces the activity of the catalyst. To counter this reduction of catalyst activity it is generally required to replenish the acid lost by entrainment. Also in the technological applications of these catalysts for vapour phase reactions measures must be taken to alleviate corrosion caused by the entrained acid in the hot gaseous reaction streams.

Acidic solid catalysts of the second type referred to above, i.e., those in which the acidity is a consequence of the composition and structure of the solid itself, do not suffer from depletion of the acidic component. Thus, acidic oxides such as tungsten oxide alone or admixed with other oxides are solid catalysts known to catalyse some of the reactions mentioned above, e.g. hydration of ethylene. Also heteropoly-acids such as silicotungstic acid on silica gel have been stated to be useful for the same purpose. Some acidic catalysts of this second type exhibit only at relatively high temperatures an appreciable activity to catalyse vapour phase chemical transformation, while others, due to their high activity, are not selective with respect to their catalytic activity even at low temperatures. Thus, for example, the relatively drastic conditions of 250°C temperature and 100 atmospheres pressure are required for the hydration of propylene to isopropanol over a silica-alumina catalyst, while the silicotungstic acid catalyst mentioned above brings about extensive polymerization of propylene when used as a catalyst in the hydration of propylene to isopropanol at a temperature exceeding 180°C. Below 180°C the catalytic activity of this catalyst is not very pronounced. It should also be noted in this context that side reactions such as coking and polymerization, which may occur with a catalyst of low selectivity, tend to cause deactivation of the catalyst with an ensuing loss in its capacity to promote the desired chemical reaction. This second type of solid acidic catalysts is thus also of limited applicability.

There are also known solid catalysts for heterogeneous reactions in which sulfuric acid and/or oxides of sulfur are supported on solid carriers. For example, a catalyst prepared by oxidizing $SO_2$ to $SO_3$ in a furnace containing the supports has been reported to promote isomerization of hydrocarbons; a catalyst prepared by soaking a porous support in dilute sulfuric acid and drying the product obtained has been reported to catalyse esterification of lower acrylic acids; a catalyst obtained by spraying a support with dilute sulfuric acid has been reported to be useful to obtain diaryl methanes; and a catalyst prepared by passing a stream of $SO_3$ through silica gel has been reported to be usful for the vapour phase hydration of olefins. All these catalysts suffer from the same drawback as those based on phosphoric acid in that the adsorbed sulfuric acid or sulfur trioxide is entrained by the gaseous phase with ensuing reduction and eventual total loss of catalytic activity. For example, it has been shown that a catalyst consisting of 12 percent by weight of sulfuric acid supported on diatomaceous earth pellets employed in the vapour phase dehydration of n-butanol to the corresponding ether completely lost its activity after 4 hours and that this loss of activity was due to the entrainment of the sulfuric acid in the vapour stream passing over the catalyst.

There are known ion exchange resins in which a sulfonic acid group is attached to a polymeric backbone such as, for example, a resin resulting from the copolymerization of vinyl sulfonic acid $CH_2=CHSO_3H$, or crotyl sulfonic acid $CH_3-CH=CHSO_3H$, with divinyl benzene as cross-linking agent. Such resins are not known to be applied in industrial practice as heterogeneous catalysts in organic reactions of the type specified hereinbefore. Attempts have been made in laboratories to use such resins as catalysts in hydration of propylene at a temperature of 135°C. However, even at this low temperature degradation of the resin due to desulfonation was reported to occur, and at a higher temperature the rate of this undesirable loss of active sites increased, leading to deactivation of the resin with concommitant decrease in the conversion of propylene to isopropanol. Moreover, due to the low permissable operative temperature all work involving use of ion exchange resins as catalysts was carried out in liquid phase with exceptionally high water-to-propylene feed ratios in the range of 10:1 to 60:1, which is an additional serious drawback in practical catalytic work.

The above drawbacks have so far imposed serious limitations of the application of heterogeneous acidic catalysis of organic reactions, notwithstanding the fact that such a catalysis, if successful, is of substantial economic advantage over homogeneous catalysis as regards regaining the catalyst and recovery of the product(s).

In accordance with the invention there is provided a composite solid catalyst for heterogeneous catalytic chemical reactions, produced by a process consisting essentially of the following steps:

a. impregnating an inert carrier with carboxymethane sulfonic acid, or a precursor thereof or precursors thereof;

b. drying the so impregnated carrier, at a temperature not exceeding 170°C to remove volatiles; and c. baking the product of step (b) at a temperature within the range of 170°–330°C to constant weight.

It is preferred to perform the impregnation described under (a) above at a temperature below 170°C. If desired, subsequent to the impregnation any residual impregnation liquors may be removed from the impregnated solid by filtration or decantation, prior to the application of step (b).

Preferably during step (b) the impregnated carrier is first heated under reduced pressure at a temperature not exceeding 138°C for about 1 hour and subsequently at 135°–145°C under atmospheric pressure for about 4 hours.

The baking in step (c) may be effected under an atmosphere of air, oxygen, hydrogen, nitrogen or another inert gas. Preferably the gas that forms the baking atmosphere is passed as a stream over the baking catalyst.

The carrier material has to be inert to any of the reactants and products under operating conditions and should remain solid under these conditions; it should preferably have a large specific surface. Examples of materials applicable as carriers are inorganic oxides such as alumina, silica, boria, zirconium dioxide, silica-alumina, silica-alumina-zirconia, various naturally occurring inorganic oxides of various grades of purity such as diatomaceous earth, atlapulgus clay, bentonite. It is also possible to use acids based on any of the above oxides as well as their salts. Also, active carbons of various origins such as animal charcoal, graphite and the like may be used.

For some carriers, such as for example, silica-alumina and naturally occurring inorganic oxides, pretreatment with an acid prior to impregnation is preferable.

The carriers may be used in the form of pellets, chips or granules for fixed bed application or in the form of small particles suitable for fluidized bed use.

As a rule the organic phase in a catalyst according to the invention will amount to 0.5 to 60 percent of the net carrier weight, the range of 10–30 percent by weight being the preferred one. The term "net carrier weight" used herein means the weight of the carrier material prior to impregnation.

It is also possible in accordance with the invention to compact a powderous catalyst according to the invention into a body of any desired shape, e.g. for the purpose of fitting it as a compact body into a specific piece of apparatus.

The impregnation of carboxymethane sulfonic acid and/or precursors thereof onto the carrier material can be effected in various ways, e.g. by spraying, adsorption from a solution or suspension, or by any other suitable technique.

For example, it is possible to impregnate the carrier with the precursors acetic anhydride and sulfuric acid and to heat the so impregnated carrier. The acetic anhydride and sulfuric acid react with each other to form acetyl sulfuric acid which through intramolecular transposition is transformed to carboxymethane sulfonic acid in accordance with the following reaction scheme:

n(CH₃.CO)₂O+ H₂SO₄=CH₃COO.SO₃H + (n-1)(CH₃CO)₂O + CH₃COOH CH₃CO.O.SO₃H→ HOOC.CH₂.SO₃H

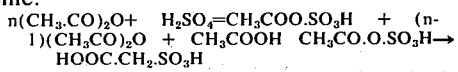

The relative proportions of the acetic anhydride and concentrated sulfuric acid in the above reaction are from 10:1 to 1:5, preferably 3:1 to 1:2.

It is of course also possible to use for the impregnation ready made acetyl sulfuric acid or a solution thereof.

Instead of using acetic anhydride and sulfuric acid it is also possible to use SO₃ in glacial acetic acid.

It is also possible to use as precursors a mixture of acetic acid and oleum.

The above precursors are named by way of example only, and quite generally any precursor(s) capable of forming carboxymethane sulfonic acid may be used.

Once the carboxymethane sulfonic acid has formed on the carrier the resulting composite is further processed as specified hereinbefore.

The chemical nature of the organic phase in the solid catalyst according to the invention has not been ascertained. It is believed that during the baking operation at least a substantial part of the carboxymethane sulfonic acid initially impregnated on the carrier or formed thereon from precursors, as the case may be, is thermally converted into different acids whose acidity is at least in part due to sulfonic acid groups.

Thus a catalyst according to the invention will as a rule contain conversion products of carboxymethane sulfonic acid, possibly in admixture with non-converted carboxymethane sulfonic acid. There may be cases in which the carboxy-methane sulfonic acid predominates.

The use of a solid acidic catalyst with free sulfonic groups as a heterogeneous catalyst in liquid or vapour phase reactions was far from obvious notwithstanding the fact that it had been known prior to this invention to use sulfonic acids as catalysts in solution, i.e. in a homogeneous system. This is so because the requirements of stability, activity, selectivity, solubility, volatility, etc. are in the case of heterogeneous catalysts at times of an entirely different order of magnitude and may even be diammetrically opposed to the same requirements in the case of a homogeneous catalyst. Thus, for example, a compound to be applied as a catalyst in solution is generally required to be soluble in the solvent used, whereas solubility of an active component of a heterogeneous catalyst in the gaseous reactants and products as well as any carrier gas, is undesirable. Furthermore, as mentioned above, polymeric sulfonic acid ion exchange resins have been shown to be impractical for heterogeneous catalysis. In view of all this it could not have been anticipated that carboxymethane sulfonic acid and its thermal conversion products, all rendered insoluble by application to a carrier as specified, will have a superior catalytic effect and consequently be useful as an improved heterogeneous catalyst.

The invention is illustrated by the following examples to which it is not limited. In these examples:

"Space Velocity" means the number of gas or liquid "volumes" calculated at NTP, passing through the catalyst bed in a specified period of time, "volume" being defined as equal to apparent volume of the catalyst bed used.

$$\text{"Percent conversion"} = \frac{\text{moles of product formed}}{\text{moles of product that form theoretically}} \times 100$$

$$\text{"Percent selectivity"} = \frac{\text{moles of product formed}}{\text{moles of reactant converted}} \times 100$$

EXAMPLE 1

Part A 150 g of Grace Grade 57 silica gel (Tayler mesh size on 6) (supplied by the Davison Division, Grace Corp.) was heated in a three-neck flask equipped with a separatory funnel under a 1 mm vacuum to 85°C (oil bath). After one hour the oil bath was removed, the silica gel was cooled to room temperature and a mixture of 298 ml of acetic anhydride and 81 ml of concentrated sulfuric acid was added in a slow stream from the separatory funnel while the silica gel was still being kept under vacuum. After half an hour the mixture was brought to atmospheric pressure, the separatory funnel was replaced by a condenser equipped with a $CaCl_2$ tube and the mixture was heated for two hours at 85°C.

Part B

The mixture was cooled, the silica gel was filtered off on a Buchner funnel without filter paper and was washed with two 30 ml portions of glacial acetic acid. The silica gel was transferred into a round-bottomed flask and was dried under a 30 mm vacuum for 1 hour on a rotary evaporator at 90°C bath temperature.

Part C

This silica gel was then transferred to a glass plate and was dried in a stream of air, first at 140°C for 4 hours, then for 30–40 hours at 200°C to constant weight. At this stage the material weighed 179.2 g.

Part D

The material was divided into three equal portions of about 60 g each. Each portion was separately charged into a 60 cm long glass reactor tube having an internal diameter of 1.8 cm. The tube was placed in a vertical oven and was steamed in a nitrogen stream in which the ratio of steam/inert gas was 1/1 (V/V), flowing at a rate of 120±20 l/hr. Steaming was started at 150°C oven temperature. Within the first eight hours the oven temperature was gradually raised to 195±5°C and steaming was continued at this temperature for 40 hours. The separately steamed portions of the now ready catalyst were combined.

The catalyst obtained had the following characteristics:

| | |
|---|---|
| Dry weight | 179.0 g |
| Gain on net carrier weight | 19.3 % |
| Apparent bulk density | 0.44 |
| Specific surface | 222±2 m²/g |

Thermogravimetric analysis (TGA) in nitrogen atmosphere:

| Temperature (°C) | Weight loss (%) |
|---|---|
| 20–500 | 19.4 |

EXAMPLE 2

150 g of silica pellets obtained from BASF under code number D11-10 and having a surface area of 121±12 m²/g were subjected to treatment as in parts A, B and C of Example 1, the heating time in part C being 100 hours. At the end of part C there was obtained 193.5 g of a grey product corresponding to 28.5 w percent gain. A portion of this product was steamed at 200°C with a nitrogen-steam mixture for 50 hours.

The catalyst obtained had the following characteristics:

| | |
|---|---|
| Gain on net carrier weight | 16.5% |
| Apparent bulk density | 0.436 |
| Specific surface | 54±5 m²/g |

Thermogravimetric analysis (TGA) in nitrogen atmosphere:

| Temperature (°C) | Weight loss (%) |
|---|---|
| 20–500 | 16.3 |

EXAMPLE 3

Part A

The procedure was as in Example 1.

Part B

The reflux condenser was replaced by a Claisen head to which a horizontal condenser, an adaptor protected with a $CaCl_2$ tube, and receiving flask were attached. The oil bath temperature was slowly raised up to 160°C. A small amount of condensate was collected while heating was continued until distillation stopped. A dry material was obtained at this stage.

Part C

The procedure was as in Example 1. At the end of this part the material obtained weighed 223 g.

Part D

The procedure was as in Example 1, and the catalyst obtained had the following characteristics:

| | |
|---|---|
| Dry weight | 208.7 g |
| Gain on net carrier weight | 39% |
| Apparent bulk density | 0.585 |
| Specific surface | 110±13 m²/g |

Thermogravimetric analysis (TGA) in nitrogen atmosphere:

| Temperature (°C) | Weight loss (%) |
|---|---|
| 20–500 | 39.5 |

EXAMPLE 4

Pretreatment 200 g of Houdry silica-alumina 511 CP (obtained from Houdry Division, Air Products and Chemicals Inc.), 4 mm × 4 mm pellets were heated in a three-neck flask equipped with a separatory funnel under a 1 mm vacuum to 85°C (oil bath). After one hour the oil bath was removed and a solution of 180 ml of concentrated sulfuric acid in 430 ml of H₂O was slowly added from the separatory funnel to the flask while the pellets were still under vacuum. After about half an hour the mixture was brought to atmospheric pressure and was heated to reflux for 2 hours. The pellets were filtered off on a Buchner funnel without filter paper, were washed free of sulfuric acid with distilled water, and were dried successively in a rotary evaporator at 20 mm and 90°C bath temperature and in an oven at 140°C. The dry, treated pellets weighed 188.4 g.

The above described treatment was repeated again on the treated pellets. This time however 428 ml of 90 percent w/w sulfuric acid was used and the mixture was heated to 140°C for 6 hours. After this treatment the pellets were again washed free of sulfuric acid with distilled water and were dried successively on a rotatory evaporator in vacuum, then for 1 hour at 140°C and for 2 hours at 200°C. The pellets weighed 184.8 g at this stage.

| | |
|---|---|
| Pretreated pellets | Al₂O₃ — 8.3% |
| Apparent Bulk Density | 0.61 |
| Original pellets (before pretreatment) | Al₂O₃ — 11.5% |
| Apparent Bulk Density | 0.63 |

150 g of the pretreated pellets were subjected to treatment as described in parts A, B and C of Example 1. At the end of the part C the procedure was continued by heating the product for 58 hours to constant weight in a stream of air at 200°C and a grey product was obtained.

The product obtained at the end of part C had the following characteristics:

| | |
|---|---|
| Dry weight | 177.2 g |
| Gain on net carrier weight | 18% |
| Specific surface | 39±6 m²/g |
| Apparent Bulk Density | 0.7 |

The product of part C above was steamed at 200±5°C for 100 hours and the resulting catalyst had the following characteristics:

| | |
|---|---|
| Dry weight | 158 g |
| Gain on net carrier weight | 6.7 % |
| Specific surface | 43±5 m²/g |
| Apparent Bulk Density | 0.69 |
| Thermogravimetric analysis (TGA) in nitrogen atmosphere: | |
| Temperature (°C) | Weight loss (%) |
| 20–500 | 7.0 |

EXAMPLE 5

200 g of Houdry 24 CP synthetic silica-alumina pellets were pretreated as described in Example 4 and there were obtained 179.6g of dry pellets having the following properties:

| | |
|---|---|
| Al₂O₃ | 2.7% |
| Specific surface | 398±45 m²/g |
| Apparent Bulk Density | 0.49 |

The original pellets before the pretreatment had the following characteristics:

| | |
|---|---|
| Al₂O₃ | 12% (Houdry data sheet) |
| Specific surface | 420 m²/g (Houdry data sheet) |
| Apparent Bulk Density | 0.48 |

150 g of the pretreated pellets were used for catalyst preparation in accordance with the process of Example 1. At the end of part C the product was heated in a stream of air at 200°C for 50 hours to constant weight and there resulted a dark grey material which had the following characteristics:

| | |
|---|---|
| Dry weight | 184.3 g |
| Gain on net carrier weight | 22.9 % |
| Apparent Bulk Density | 0.58 |

This material was steamed for 80 hours at 200± 5°C and the resulting catalyst had the following characteristics:

| | |
|---|---|
| Supported phase concentration | 11.1 % |
| Apparent Bulk Density | 0.55 |
| Specific surface | 164±21 m²/g |
| Thermogravimetric analysis (TGA) in nitrogen atmosphere: | |
| Temperature (°C) | Weight loss (%) |
| 20–500 | 11.3 |

EXAMPLE 6

123 g of glacial acetic acid was heated to 110°–120°C with magnetic stirring in a three neck flask while a stream of sulfur trioxide was introduced for 5 hours. By the end of this period, a 29.6 g weight gain was obtained in the contents of the flask. This solution was added in vacuo to 100 g of preheated pellets of a diatomaceous earth sold under the trademark Celite and the mixture was then kept at atmospheric pressure and room temperature for a quarter of an hour and subsequently heated to 80°C for 1½ hours. The volatile material was distilled off at 160°C (oil bath temperature) and the pellets were baked at 200°C for 15 hours in a stream of air. The resulting catalyst weighed 129 g corresponding to 29 percent gain on the net carrier weight.

EXAMPLE 7

10 g of predried microspherical silica gel (obtained from Davison Division, Grace Corp.) (particle size 30 to 40 mesh Tayler scale) was placed in an evacuated flask, a mixture of 40 ml of acetic anhydride and 10.8 ml of concentrated sulfuric acid was added, and the mixture was heated at atmospheric pressure at 85°C for 4 hours. After cooling the mixture, the solid was filtered off, washed with two 8 ml portions of glacial acetic acid and dried in a rotary evaporator in a 30 mm Hg vacuum at 80°C for 1 hour. The material was then heated at 140°C in a stream of air for 6 hours and was baked at 200°C to constant weight. The resulting catalyst was a black microspherical product containing 89 percent by weight of material derived from the carrier. This catalyst is suitable for fluidized bed applications.

EXAMPLE 8

The catalyst prepared in accordance with Example 1 was used for the production of isopropanol by catalytic hydration of propylene. A fixed bed of 50 ml of the catalyst was established in a high pressure flow reactor system and the reaction was carried out under the following conditions:

| | |
|---|---|
| Temperature | 172–177°C |
| Pressure | 135–138 PSIA |
| Space Velocity (number of volumes of gas at NTP passing over the catalyst column) | 1900–2300 Hr$^{-1}$ |
| Water to propylene mole ratio | 0.7:1.0 – 1.0:1.0 |

In a 119 hour continuous run test conditions were readjusted every 10 hours and isopropanol was obtained in 7.1 to 9.4 mole percent conversions (calculated on propylene) in the form of 20.4 to 35.0 weight percent aqueous solutions. In all tests, no by-products were detectable by gas chromatographic analysis in the isopropanol product solutions, and in the gaseous material leaving the reactor system. The accuracy limit of the gas chromatography analytical method lies at about 10 ppm and therefore any by-products such as acetone, n-propanol or propylene olygomers were present, if at all, in quantities less than 10 ppm. The test conditions and results are given in the following Table:

TABLE

| Temp. °C | Press. PSIA | S.V. Hr$^{-1}$ | $H_2O$/ $C_3H_8$ mole/mole | Conv. to Isopropanol % conversion | Conc. of Isopropanol in aq. sol. Weight % |
|---|---|---|---|---|---|
| 172 | 135 | 1900 | 0.7:1.0 | 7.1 | 20.4 |
| 175 | 136 | 2050 | 0.8:1.0 | 8.3 | 28 |
| 177 | 138 | 2300 | 0.9:1.0 | 8.8 | 34 |
| 177 | 138 | 2050 | 0.9:1.0 | 9.4 | 32 |
| 177 | 138 | 2000 | 1.0:1.0 | 9.1 | 35 |

EXAMPLE 9

Catalytic hydration of propylene to isopropanol was carried out using a catalyst prepared in accordance with Example 2 in a 50 ml fixed bed, in a similar reactor as in Example 8, under the following conditions:

| | |
|---|---|
| Temperature | 174–181°C |
| Pressure | 105–135 PSIA |
| Space Velocity | 500–1700 Hr$^{-1}$ |
| Water to propylene mole ratio | 0.0:1.0 – 1.3:1 |

In a continuous 95 hour run test conditions were readjusted every 10 hours and isopropanol was obtained in 6.6 to 8.9 mole percent conversions (calculated on propylene) in the form of 15 to 27 weight percent aqueous solutions. The selectivity to isopropanol was 91 to 96 percent with isopropyl ether present as by-product.

EXAMPLE 10

The catalytic hydration of propylene to isopropanol was carried out in a similar reactor system as in Example 8 using a 50 ml bed of a catalyst prepared according to Example 3. The conditions were as follows:

| | |
|---|---|
| Temperature | 174–187°C |
| Pressure | 130–135 PSIA |
| Space Velocity | 1700–2200 Hr$^{-1}$ |
| Water to propylene mole ratio | 0.5:1.0 – 0.8:1.0 |

In a 25 hour run test conditions were readjusted every 10 hours and isopropanol was obtained in 6.0 to 8.1 mole percent conversions (calculated on propylene) in the form of 19.3 to 30.2 weight percent aqueous solutions. The selectivity was 94 to 98 percent with isopropyl ether being present as by-product.

EXAMPLE 11

200 g of silica-alumina pellets containing 11.5 percent by weight of $Al_2O_3$ were placed in a solution prepared from 108 ml of concentrated sulfuric acid and 430 ml of water, and the solution was refluxed for 2 hours. The pellets were filtered off, washed with distilled water to neutral pH and were thoroughly dried at 140°C. After this treatment the alumina content of the pellets were reduced to 8.3 percent.

A catalyst was prepared from these pretreated pellets using the procedure of Example 1 and the resulting catalyst had a specific surface of 43±5 m$^2$/g.

The catalyst was used for the catalytic hydration of ethylene to ethanol employing a 50 ml fixed bed in the same reactor system as in Example 8, under the following conditions:

| | |
|---|---|
| Temperature | 169–180°C |
| Pressure | 104–134 PSIA |
| Space Velocity | 930–1840 Hr$^{-1}$ |
| Water to ethylene mole ratio | 0.4:1.0 – 1.2:1.0 |

In a 181 hour run test conditions were readjusted every 10 hours and 2.0 to 4.1 mole percent conversions of ethylene to ethanol were obtained. Ethanol was obtained in the form of 7.6 to 14.2 weight percent aqueous solutions. Selectivity was 92 to 98 percent, with ethyl ether being obtained as by-product. All product analyses were performed by gas chromatography.

EXAMPLE 12

Using the same reactor system as in Example 8 with a 50 ml charge of the catalyst prepared in accordance with Example 1 the hydration of ethylene to ethanol was carried out under the following conditions:

| | |
|---|---|
| Temperature | 195–205°C |
| Pressure | 175–185 PSIA |
| Space Velocity | 1750 to 1850 Hr$^{-1}$ |
| Water to ethylene mole ratio | 1.45:1.0–1.55:1.0 |

In a 140 hour continuous run test conditions were readjusted every 10 hours and 2.0 to 2.2 mole percent ethylene to ethanol conversions were obtained. Ethanol was obtained in the form of 3.1 to 3.3 weight percent aqueous solutions. Selectivity was 98 to 99 percent, with ethyl ether present in trace quantities as a by-product.

EXAMPLE 13

The catalyst of Example 1 was used for the catalytic formation of isopropyl acetate from acetic acid and propylene. The reaction was carried out at atmospheric pressure using a vertical reactor charged with 30 ml of the catalyst. The reaction conditions were:

| | |
|---|---|
| Temperature | 130–180°C |
| Pressure | 1 atm |
| Space Velocity | 800–2100 Hr$^{-1}$ |
| Propylene to acetic acid mole ratio | 1.1:1.0 – 3.5:1.0 |

In a continuous run of 47 hours test conditions were readjusted every 5 hours and 14 to 25 mole percent acetic acid to isopropyl acetate conversions were obtained. Isopropyl acetate was obtained in the form of 20 to 40 percent solutions in acetic acid. Selectivity was 100 percent in all runs below 150°C reactor temperature. When the temperature was higher a small amount of propylene dimers and trimers were present in the product. All analyses were performed by gas chromatography.

EXAMPLE 14

The experiment of Example 13 was repeated using the catalyst described in Example 3. The conditions were as in Example 13 and the conversions of acetic acid to isopropyl acetate were comparable. However at temperatures above 150°C increased quantities of propylene olygomers were obtained as by-products.

EXAMPLE 15

Catalytic formation of anisole by the reaction of phenol with methanol in the gaseous phase was performed with the catalyst of Example 2 using a vertical reactor charged with 30 ml of the catalyst. The reaction conditions were:

| | |
|---|---|
| Temperature | 170–195°C |
| Pressure | 1 atm |
| Liquid space velocity | 0.8–2.8 Hr$^{-1}$ |
| Phenol to methanol mole ratio | 1.0:1.0 – 1.0:2.5 |

In a 26 hour run test conditions were readjusted every 4 hours and 12.5 to 28.3 moles percent conversions of phenol to anisole were obtained. Anisole was obtained in 100 percent selectivity and analyses were performed by gas chromatography.

EXAMPLE 16

Gaseous phase alkylation of benzene by propylene to cumene was performed using the catalyst of Example 3. The experiment was carried out in a vertical reactor charged with 30 ml catalyst. The reaction conditions were:

| | |
|---|---|
| Temperature | 195–205°C |
| Pressure | 1 atm |
| Liquid space velocity (benzene) | 1.7–3.5 Hr$^{-1}$ |
| Benzene to propylene mole ratio | 2.0:1.0 – 4.5:1.0 |

In 5 separate 7 hour runs 3.5 to 5.2 mole percent conversions of benzene to cumene were obtained. Selectivity to cumene was 67 to 94 percent with ortho- and meta- disopropyl benzenes obtained as by-products.

I claim:

1. A composite solid catalyst for heterogeneous catalytic chemical reactions, produced by a process consisting essentially of the following steps:
   a. impregnating an inert carrier with carboxymethane sulfonic acid, a precursor thereof or precursors thereof which form carboxymethane sulfonic acid on heating;
   b. drying the so-impregnated carrier, at a temperature not exceeding 170°C, to remove volatiles; and
   c. baking the product of step (b) at a temperature within the range of 170°–330°C to constant weight.

2. A catalyst according to claim 1, wherein said carrier is an inorganic oxide, an acid based on such oxide or a salt thereof.

3. A catalyst according to claim 1, wherein the carrier is silica-alumina.

4. A catalyst according to claim 1, wherein the carrier is an active carbon or graphite.

5. A catalyst according to claim 1, wherein the carrier is a diatomaceous earth.

6. A catalyst according to claim 1, wherein said precursors are acetic acid anhydride and sulfuric acid.

7. A catalyst according to claim 1, wherein said precursors are glacial acetic acid and sulfur trioxide.

8. A catalyst according to claim 1, wherein said precursors are acetic acid and oleum.

9. A catalyst according to claim 1, wherein acetylsulfuric acid is used as precursor.

* * * * *